(12) United States Patent
Timmons et al.

(10) Patent No.: US 6,329,024 B1
(45) Date of Patent: *Dec. 11, 2001

(54) METHOD FOR DEPOSITING A COATING COMPRISING PULSED PLASMA POLYMERIZATION OF A MACROCYCLE

(75) Inventors: Richard B. Timmons; Yuliang Wu, both of Arlington, TX (US)

(73) Assignee: Board of Regents, The University of Texas System, Austin, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/316,620

(22) Filed: May 21, 1999

Related U.S. Application Data

(63) Continuation-in-part of application No. 09/115,860, filed on Jul. 15, 1998, which is a continuation-in-part of application No. 08/632,935, filed on Apr. 16, 1996, now Pat. No. 5,876,753.
(60) Provisional application No. 60/055,260, filed on Aug. 8, 1997.

(51) Int. Cl.[7] ................................................ C08J 7/18
(52) U.S. Cl. ................ 427/491; 427/164; 427/255.6; 427/294; 427/492; 427/569; 427/575; 427/580; 427/582
(58) Field of Search ................ 427/491, 492, 427/569, 575, 580, 582, 164, 255.6, 294

(56) References Cited

U.S. PATENT DOCUMENTS

| | | |
|---|---|---|
| 3,008,920 | 11/1961 | Urchick . |
| 3,070,573 | 12/1962 | Beck . |
| 3,854,982 | 12/1974 | Aelion et al. . |
| 3,916,033 | 10/1975 | Merrill . |
| 3,925,178 | 12/1975 | Gesser et al. . |
| 3,939,049 | 2/1976 | Ratner et al. . |
| 4,143,949 | 3/1979 | Chen . |
| 4,311,573 | 1/1982 | Mayhan et al. . |
| 4,585,666 | 4/1986 | Lambert . |

(List continued on next page.)

FOREIGN PATENT DOCUMENTS

| | | |
|---|---|---|
| 195 48 152 A1 | 12/1995 | (DE) . |
| 195 48 152 | 6/1997 | (DE) . |
| 0 574 352 A1 | 2/1993 | (EP) . |
| 63 075002 | 8/1988 | (JP) . |
| WO 87 01040 | 2/1987 | (WO) . |
| PCT/US90/05032 | 9/1990 | (WO) . |
| WO 95 04609 | 2/1995 | (WO) . |
| WO 97 22631 | 6/1997 | (WO) . |
| WO 97 38801 | 10/1997 | (WO) . |

OTHER PUBLICATIONS

H. Yasuda and T. Hsu, "Some Aspects of Plasma Polymerization Investigated by Pulsed R.F. Discharge," Journal of Polymer Science, vol. 15, 1997, pp. 81–97 (No month avail.).

(List continued on next page.)

*Primary Examiner*—Bernard Pianalto
(74) *Attorney, Agent, or Firm*—Jackson Walker L.L.P.

(57) ABSTRACT

Devices, and their method of production, having coatings deposited by pulsed plasma polymerization of a macrocycle containing a heteroatom, wherein the heteroatom is oxygen, nitrogen, sulfur, or a mixture thereof. The coatings on contact lens are preferably deposited by gas phase polymerization of a cyclic ether, such as crown ether, which coatings are non-fouling and wettable, and the gas phase polymerization utilizes a pulsed discharge.

10 Claims, 11 Drawing Sheets

(a)

U.S. PATENT DOCUMENTS

| | | |
|---|---|---|
| 4,589,964 | 5/1986 | Mayhan et al. . |
| 4,656,083 | 4/1987 | Hoffman et al. . |
| 4,693,799 | 9/1987 | Yanagihara et al. . |
| 4,880,687 | 11/1989 | Yokoyama et al. . |
| 4,919,659 * | 4/1990 | Horbett et al. . |
| 5,002,974 | 3/1991 | Geria . |
| 5,007,928 | 4/1991 | Okamura et al. . |
| 5,034,265 | 7/1991 | Hoffman et al. . |
| 5,091,204 | 2/1992 | Ratner et al. . |
| 5,153,072 | 10/1992 | Ratner et al. . |
| 5,171,267 | 12/1992 | Ratner et al. . |
| 5,196,458 | 3/1993 | Nunez et al. . |
| 5,304,584 | 4/1994 | Nunez et al. . |
| 5,451,428 | 9/1995 | Rupp . |
| 5,630,946 | 5/1997 | Hart et al. . |

OTHER PUBLICATIONS

Gabriel P. Lopez, Buddy D. Ratner, Caren D. Tidwell, Claire L. Haycox, Richard J. Rapoza and Thomas A. Horbett, "Glow Discharge Plasma Deposition of Tetraethylene Glycol Dimethyl Ether for Fouling–Resistant Biomaterial Surfaces," Journal of Biomedical Materials Research, vol. 26, 1992, pp. 415–439 (No month avail.).

V. Panchalingam, Bryan Poon, Hsiao–hwei Huo, Charles R. Savage, Richard B. Timmons and Robert C. Eberhart, "Molecular Surface Tailoring of Biomaterials via Pulsed EF Plasma Discharges," J. Biomater Sci. Polymer Edn., vol. 5, No. 1/2, 1993, pp. 131–145 (No month avail.).

V. Panchalingam, X. Chen, Charles R. Savage, Richard B. Timmons and Robert C. Eberhart, "Molecular Tailoring of Surfaces via Pulsed RF Plasma Depositions," Journal of Applied Polymer Science: Applied Polymer Symposium 54, 1994, pp. 123–141 (No month avail.).

Dierk Beyer, Wolfgang Knoll, Helmut Ringsdorf, Jenn–Hann Wang, Richard B. Timmons, and Peter Sluka, "Reduced Protein Adsorption on Plastics via Direct Plasma Deposition of Triethylene Glycol Monoallyl Ether," 1997 John Wiley & Sons, Inc., pp. 181–189 (No month avail.).

E.E. Johnston, B.D. Ratner and J.D. Bryers, "RF Plasma Deposited PEO–Like Surfaces that Inhibit Pseudomonas Aruginosa Accumulation," Polymeric Materials Science and Engineering, vol. 77, 1997, p. 577. (No month avail.).

K. Nakajima, A.T. Bell and M. Shen. "Plasma Polymerization of Tetrafluoroethylene," Journal of Applied Polymer Science. vo. 23, 1979, pp. 2627–2637 (No month avail.).

E.E. Johnston, B.D. Ratner and J.D. Bryers, "RF Plasma Deposited PEO–Like Films: Surface Characterization and Inhibition of Pseudomonas Aeruginosa Accumulation." Plasma Processing of Polymers, vol. 346, 1997, p. 465–476. (No month avail.).

* cited by examiner (a)

(b)

(a)

(b)

METHOD FOR DEPOSITING A COATING COMPRISING PULSED PLASMA POLYMERIZATION OF A MACROCYCLE

This is a continuation-in-part application of prior U.S. patent application Ser. No. 09/115,860, filed Jul. 15, 1998, which is a continuation-in-part application of prior U.S. patent application Ser. No. 08/632,935, now U.S. Pat. No. 5,876,753 filed Apr. 16, 1996, and which claims the benefit of U.S. Provisional Application Ser. No. 60/055,260, filed Aug. 8, 1997, entitled "NON-FOULING WETTABLE COATED DEVICES," each of which is commonly assigned with the present invention and the entire content of each of which is hereby incorporated by reference.

The U.S. Government has certain rights in the present invention pursuant to the National Institutes of Health under Grant R01 AR43186 and by the State of Texas through the Texas Higher Education Coordinating Board ATP Program under Grant 003657-137.

BACKGROUND

This invention relates to devices having coatings deposited thereon and their method of production. Specifically, this invention relates to devices, and their method of production, having coatings deposited by pulsed plasma polymerization of a macrocycle containing a heteroatom, wherein the heteroatom is oxygen, nitrogen, sulfur, or a mixture thereof. More specifically, this invention relates to devices, and their method of production, having coatings deposited by gas phase polymerization of a cyclic ether, which coatings are non-fouling and wettable, and the gas phase polymerization utilizes a pulsed discharge.

Non-biologically fouling, wettable thin film surface coatings are of interest for use in improving the biocompatibility of contact lenses. Coatings containing ethylene oxide ($-CH_2-CH_2-O)_n$ ("EO") units are quite effective in providing non-fouling, relatively hydrophilic surfaces. In particular, it has been recently demonstrated that under continuous-wave conditions, volatile, low molecular weight molecules containing relatively few EO units can be plasma polymerized onto surfaces to provide wettable, non-fouling thin film coatings [G. P. Lopez, B. D. Ratner, C. D. Tidwell, C. L. Haycox, R. J. Rapoza, and T. A. Horbett, "Glow discharge plasma deposition of tetraethylene glycol dimethyl ether for fouling-resistant biomaterial surfaces," *J. Biomed. Mater. Res.*, 26,415–439 (1992). D. Beyer, W. Knoll, H. Ringsdorf, J.-H. Wang, R. B. Timmons, and P. Sluka, "Reduced protein adsorption on plastics via direct plasma deposition of triethylene glycol monoallyl ether," *J. Biomed. Mater. Res.*, 36, 181–189 (1997)]. U.S. patent application Ser. No. 09/115,860 disclosed that monomers containing as few as two EO units per molecule, when plasma polymerized under low power input conditions made available by the variable duty cycle pulsed plasma technique, yielded strongly adherent, wettable, and non-fouling coatings when deposited on the surfaces of contact lenses. The monomers employed involved only non-cyclic linear or branched olefinic compounds.

Cyclic ethers, more commonly referred to as crown ethers, represent a separate class of EO molecules containing several oxygen atoms, usually in a regular pattern. Recent reports have shown that continuous-wave plasma polymerization of these compounds can provide surface coatings which exhibit a modest level of biomolecule rejection [E. E. Johnston, B. D. Ratner, and J. D. Bryers, "RF plasma deposited PEO-like surfaces that inhibit *Pseudomonas aeruginosa* accumulation," *Polym. Mater. Sci. and Engi.* (Abstracts), 77, p. 577 (1997). E. E. Johnston and B.D. Ratner, "The effects of linear and cyclic precursors on the molecular structure of ether-rich plasma-deposited films," *Mater. Res. Soc.* (Abstracts), p. 464, December 1998 (Boston, Mass.); E. E. Johnston, B. D. Ratner and J. D. Bryers, NATO ASI Series E, Applied Science, Vol 346, pp.465–476, (1997)]. In this work, reduced fouling was demonstrated with measurements of *Pseudomonas aeruginosa* adherence to plasma modified surfaces versus uncoated glass surfaces. For example, an approximate 40% reduction in *Ps. Aeruginosa* adherence was observed on plasma polymerized 12-crown-4 ($C_8H_{16}O_4$) surfaces relative to that observed with uncoated glass, as estimated from the graphic data provided [E. E. Johnston, B. D. Ratner, and J. D. Bryers, "RF plasma deposited PEO-like surfaces that inhibit *Pseudomonas aeruginosa* accumulation,"*Polym. Mater. Sci. and Engi.* (Abstracts), 77, p. 577 (1997)]. Slightly higher reduction in adsorbed bacteria (i.e., a few percent higher) was reported on coatings obtained from the plasma polymerization of 15-crown-5 ($C_{10}H_{20}O_5$). The level of protein adsorption was observed to be independent of the power input provided during the plasma polymerization of this monomer. Additionally, the crown ether compounds were shown to be considerably less efficacious than coatings obtained from linear, saturated EO containing molecules (commonly referred to as glymes) of general formula $CH_3(OCH_2CH_2)_nOCH_3$. For example, tetraglyme ($C_{10}H_{22}O_5$) was shown to reduce *Ps. Aeruginosa* surface adsorption by a factor of at least five times more than that observed with the comparable molecule weight 15-crown-5 monomer. Furthermore, the tetraglyme coatings deposited at higher plasma power (20 W) were shown to adsorb less bacteria than that obtained on coatings deposited at 5 W [E. E. Johnston, B. D. Ratner, and J. D. Bryers, "RF plasma deposited PEO-like surfaces that inhibit *Pseudomonas aeruginosa* accumulation," *Polym. Mater. Sci. and Engi.* (Abstracts), 77, p. 577 (1997)]. Thus, in summary, the reported work showed that: (1) The accumulation of bacteria onto the linear glyme films was much lower than that on the crown ether films, indicating that cyclic ethers produce significantly poorer non-fouling coatings than the linear glyme molecules when deposited as plasma polymer films on substrates; and (2) the efficacy of the plasma films in functioning as non-fouling coatings is either independent of the power employed during the plasma deposition (as shown for cyclic ethers) or they become less efficacious with decreasing power (as shown for the linear glyme).

Additional notable aspects of the prior studies is that samples to be coated were located upstream of the plasma discharge zone, apparently in order to improve retention of the EO content in the plasma films [E. E. Johnston, B. D. Ratner, and J. D. Bryers, "RF plasma deposited PEO-like surfaces that inhibit *Pseudomonas aeruginosa* accumulation," *Polym. Mater. Sci. and Engi.* (Abstracts), 77, p. 577 (1997); E. E. Johnston, B. D. Ratner and J. D. Bryers, NATO ASI Series E, Applied Science, Vol 346, pp. 465–476, (1997)]. Also, a relatively high (80 W) initial deposition was employed to provide a sub-surface which was apparently required to enhance adhesion of the subsequent outermost layers deposited at lower power inputs [E. E. Johnston, B. D. Ratner, and J. D. Bryers, "RF plasma deposited PEO-like surfaces that inhibit *Pseudomonas aeruginosa* accumulation," *Polym. Mater. Sci. and Engi.* (Abstracts), 77, p. 577 (1997); E. E. Johnston, B. D. Ratner and J. D. Bryers, NATO ASI Series E, Applied Science, Vol 346, pp. 465–476, (1997)].

SUMMARY

The present invention is directed to a device having a substrate and a coating composition, the coating composition being formed by polymerization of a gas consisting of at least one macrocycle which contains, besides carbons and hydrogens, at least one hetero atom, wherein the gas polymerization utilizes a pulsed discharge and wherein the hetero atom is oxygen, nitrogen or sulfur. The macrocycle can be a cyclic ether, such as an ethylene oxide, a dioxane, a crown ether, or a mixture thereof.

The present invention is also directed to a method for plasma depositing a coating to a solid substrate by subjecting a macrocycle to a gas phase polymerization utilizing a pulsed discharge.

DETAILED DESCRIPTION

Figure 1:
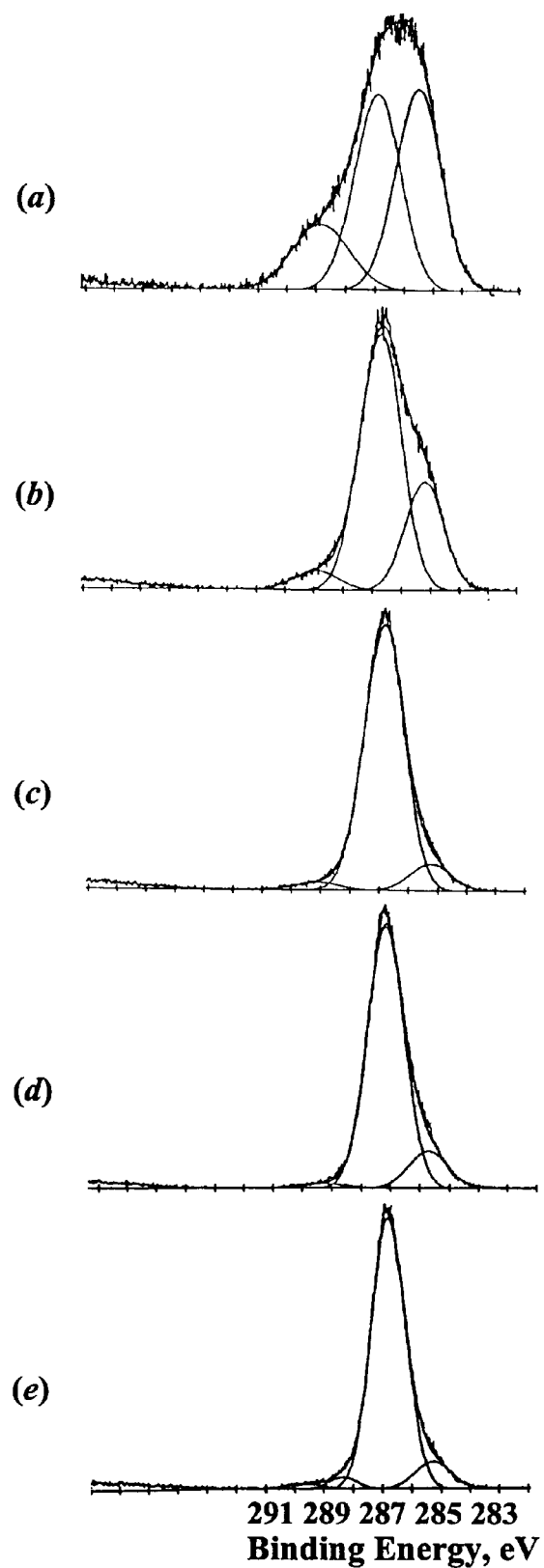
FIG. 1(a, b, c, d and e) show high resolution C(1s) ESCA spectra of 12-crown-4 films plasma polymerized at 25 W peak power. RF duty cycle (on/off times or on/off ratio in ms) employed during formation of each film are: (a) 0.1/1; (b) 0.1/2; (c) 0.1/4; (d) 0.1/8; and (3) 0.1/12.

Broadly, the present invention pertains to a device having a substrate and a coating composition, the coating composition being formed by a gas phase polymerization of a gas consisting of at least one macrocycle which contains at least one hetero atom, wherein the gas polymerization utilizes a pulsed discharge and wherein the hetero atom is oxygen, nitrogen or sulfur.

A macrocycle is a cyclic compound containing, besides carbon and hydrogen atoms, at least one hetero atom, such as, oxygen, nitrogen, sulfur, or a mixture thereof. A macrocycle can be monocyclic, bicyclic or cycles of higher order. Bicyclics and cycles of higher order include cryptans and spherands. A preferred macrocycle of the present invention includes a cyclic ether, such as ethylene oxide, dioxane, and crown ether. More preferably, the macrocycle of the present invention includes crown ether. Crown ethers are monocyclic and are relatively large-ring compounds of carbons and hydrogens containing several oxygen atoms, usually in a regular patterns. Examples or crown ethers include 12-crown-4, 15-crown-5, 18-crown-6, dicyclyhexano-18-crown-6, 4'-aminobenzyl-15-crown-5, 2-(aminomethyl)-12-crown-4, 2-(aminomethyl)-15-crown-5, 2-(aminomethyl)-18-crown-6, 1-aza- 12-crown-4, 1-aza-15-crown-5, 1-aza-18-crown-6, benzo-12-crown-4, benzo- 15-crown-5, benzo-18-crown-6, bis[(benzo-15-crown-5)-15-ylmethyl]pimelate, 4'bromobenzo-18crown-6, dibenzo-18-crown-6, dibenzo-24-crown-8, dibenzo-30-crown-10, ar,ar'-di-tert-butyldibenzo-18-crown-6, dicyclohexano-24-crown-8, 4'-formylbenzo-15-crown-5, 2-(hydroxytmethyl)-12-crown-4, 2-(hydroxymethyl)-15-crown-5, 2-(hydroxymethyl)-18-crown 6, 4'nitrobenzo-15-crown-5, and poly[(dibenzo-18-crown-6)-co-formaldehyde].

The present invention also pertains to a method for plasma depositing a coating to a solid substrate by subjecting a macrocycle to a gas phase polymerization utilizing a pulsed discharge. The solid substrate of the present invention can be contact lens or biomaterials, such as medical implants.

In one embodiment, the present invention pertains to the plasma polymerization of a cyclic ether, such as a crown ether, as a potential route for synthesis of wettable, non-fouling coatings, with a particular focus on applying these films to contact lenses. In contrast with the continuous-wave plasma operational mode employed in prior studies of crown ethers [E. E. Johnston, B. D. Ratner, and J. D. Bryers, "RF plasma deposited PEO-like surfaces that inhibit *Pseudomonas aeruginosa* accumulation," *Polym. Mater. Sci. and Engi.* (Abstracts), 77, p. 577 (1997). E. E. Johnston and B.D. Ratner, "The effects of linear and cyclic precursors on the molecular structure of ether-rich plasma-deposited films," *Mater. Res. Soc.* (Abstracts), p. 464, December 1998 (Boston, Mass.); E. E. Johnston, B. D. Ratner and J. D. Bryers, NATO ASI Series E, Applied Science, Vol 346, pp. 465–476, (1997)], pulsed plasma polymerizations were employed here. As an important example of the pulsed plasma approach, it was noted that it was possible to deposit wettable, adherent, and non-fouling coatings from the monomer 12-crown-4 under a pulsed plasma duty cycle of 0.1 ms plasma on, 8 ms plasma off, and 25 W peak power. From the equation given below, this corresponds to an average power input of only 0.31 W. Thus pulsed plasma technique of this invention offers the substantial advantage of depositing plasma films at average power inputs which are significantly below usable values under continuous-wave conditions. By way of comparison, it was noted that using the same reactor and identical monomer flow rate and pressure as employed during the pulsed run, a minimum of 6 W power input was required to obtain a sustained plasma discharge and film formation. For reasons documented below, the ability to deposit high-quality plasma films at ultra low power inputs is of pivotal importance in obtaining more efficacious non-fouling, highly wettable coatings in films obtained from the crown ethers.

Detailed studies were carried out using the monomers dioxane (nominally 6-crown-2), 12-crown-4, and 15-crown-5. Films obtained were characterized by X-ray photoelectron spectroscopy (XPS) and Fourier transform infrared spectroscopy (FT-IR). Surface wettabilities were measured using a Ramé-Hart goniometer and the static sessile drop water contact angle method. The UV-visible transmission spectra of the plasma films were also recorded via deposition of the samples on quartz plates. The adherence and stability of the plasma films were measured using a variety of methods, including prolonged soaking, extended exposure to flow, and abrasive cleaning using common commercial cleansers. The non-fouling properties of the coatings were examined via measurements of protein surface adsorption using radio-labeled proteins.

Studies were carried out in which the above-noted film properties were examined as a function of the pulsed plasma duty cycles employed during film formation. With all monomers examined, an enhanced retention of the EO content of the starting monomers was observed in the plasma films as the plasma power employed during film formation was decreased. The relationship between film EO content and average power input was found to be highly non-linear in nature, with particularly dramatic (and advantageous) compositional changes observed at the ultra low power inputs available under pulsed, but not continuous-wave, deposition conditions. The structure composition and properties of the plasma films were found to vary in relatively similar fashion for all three monomers studied.

The plasma reactor and general operating conditions were similar to those previously described [V. Panchalingam, X. Chen, C. R. Savage, and R. B. Timmons, "Molecular tailoring of surfaces via pulsed RF plasma depositions," *J. Appl. Polym. Sci.: Appl. Polym. Symp.*, 54, 123–141 (1994)]. and successfully employed in prior generation of wettable, non-fouling coatings using olefinic EO containing monomers [D. Beyer, W. Knoll, H. Ringsdorf, J.-H. Wang, R. B. Timmons, and P. Sluka, "Reduced protein adsorption on plastics via direct plasma deposition of triethylene glycol monoallyl ether," *J. Biomed. Mater. Res.*, 36, 181–189 (1997)].

In this method, coatings are deposited on solid substrates via plasma polymerization of selected monomers under controlled conditions. The plasma is driven by RF radiation using coaxial external RF electrodes located around the exterior of a cylindrical reactor. Substrates to be coated are preferably located in the reactor between the RF electrodes; however, substrates can be located either before or after the electrodes. The reactor is evacuated to background pressure using a rotary vacuum pump. A fine metering valve is opened to permit vapor of the monomer (or monomer mixtures) to enter the reactor. The pressure and flow rate of the monomer through the reactor is controlled by adjustments of the metering valve and a butterfly control valve (connected to a pressure controller) located downstream of the reactor. In general, the monomer reactor pressures employed range from approximately 50 to 200 mili-torr, although values outside this range can also be utilized. It is preferred that the compounds have sufficiently high vapor pressures so that the compounds do not have to be heated above room temperature (from about 20 to about 25° C.) to vaporize the compounds. Although the electrodes are located exterior to the reactor, the process of the invention works equally well for electrodes located inside the reactor (i.e. a capacitively coupled system).

The chemical composition of a film obtained during plasma deposition is a strong function of the plasma variables employed, particularly the RF power used to initiate the polymerization processes. It is preferred to operate the plasma process under pulsed conditions, compared to continuous wave ("CW") operation, because it is possible to employ reasonably large peak powers during the plasma on initiation step while maintaining a low average power over the course of the coating process. Pulsing means that the power to produce the plasma is turned on and off. The average power under pulsing is defined as:

$$\text{Average Power} = \frac{\text{plasma-on time}}{\text{plasma-on time} + \text{plasma-off time}} \times \text{Peak Power}$$

For example, a plasma deposition carried out at a RF duty cycle of 10 msec on and 200 msec off and a peak power of 25 watts corresponds to an average power of 1.2 watts. The Peak Power is preferably between about 10 and about 300 watts.

The formal definition of duty cycle is defined as the ratio of the plasma on time (i.e. discharge time) to a sum of the plasma-on time and the plasma-off time (i.e. non-discharge time), as represented below:

$$\text{Duty cycle} = \frac{\text{plasma-on time}}{\text{plasma-on time} + \text{plasma-off time}}$$

However, for convenience, the plasma on to plasma off times are frequently cited herein as a simple ratio of on to off time, both times employing the same scale (i.e. milliseconds or microseconds).

The workable range of duty cycle is less than about ⅕, the preferred range is between about 1/10 and about 1/1000, and the more preferred range is between about 1/10 and about 1/100. The plasma-on time should be larger than about 1 µsec, preferably in the range of between about 10 µsec and about 100 msec, and more preferably in the range of between about 100 µsec and about 10 msec. The plasma off time, i.e. the non-discharge time, should be larger than about 4 µsec, preferably in the range of between about 100 µsec and 2000 msec, and more preferably in the range of between about 200 µsec and about 100 msec. The total deposition time varies depending on the monomer and the conditions used. Typically, the deposition time can vary from about 0.5 min to about 3 hours.

Pulsed plasma deposition permits use of relatively high peak powers while simultaneously maintaining relatively low average powers which provides for the retention of monomer functional groups. Coating compositions deposited under low average power pulsed conditions tend to be more adhesive to a given substrate when compared to films deposited at the same average power but under CW operation. For a given average power, the momentary high peak power available under pulsed conditions apparently assists in obtaining a stronger grafting of the film to the substrate than that obtained under the same average power CW conditions.

For a given RF peak power, an increased retention of the ether content (C—O functionality) of the plasma generated coating is observed as the plasma duty cycle is reduced when working with a given monomer. Alternatively, the chemistry of the coating composition can be varied under pulsed conditions by working at a single plasma duty cycle but varying peak powers. There is an increased incorporation of C—O functionality in coating compositions as the peak power is decreased. Surprisingly, the plasma generated film composition can be varied by changing the plasma on to plasma off pulse widths, at a fixed ratio of plasma on to plasma off times and at a fixed RF peak power. Although the film deposition mode described is one of RF plasma polymerization, those familiar in the art will recognize that other polymerization methods (e.g., microwave plasmas, photo-polymerization, ionizing radiation, electrical discharges, etc.) could also be adapted for this purpose.

The chemical composition of the films of this invention can be varied during pulsed plasma deposition, by varying the peak power and/or the duration of the plasma on and plasma off pulse widths. This excellent film chemistry controllability is achieved without recourse to modulating the temperature of the substrate during the actual coating process. To produce a coating composition with the preferred ratio of C—O functionality to C—C functionality, it is preferred that the average power of the pulsed plasma deposition is less than about 100 watts, more preferably less than about 40 watts, most preferably less than about 5 watts. The highest ratios of C—O functionality to C—C functionality can be obtained when the average power is 1 watt and less which provides the most non-fouling and wettable coating compositions. The average pulsed powers used in this invention are less than the wattage under CW conditions in a similar reactor configuration.

However, as those skilled in the art will recognize, the actual effect of peak power input on film composition is dependent on the reactor volume (i.e. power density). In the present invention, the reactor volume is approximately 2 liters. Obviously, if a smaller reactor were employed, the same film composition changes reported herein would be achieved at lower peak power inputs. Other reaction variables which would influence peak power inputs are reactor pressure and monomer(s) flow rates. If larger reactor volumes were employed, the same film compositional variations could be achieved using higher power input.

The use of lower average power conditions increases the presence of functional groups, e.g. ether units, in the coatings, but the less energetic deposition conditions at lower average power may result in poorer adhesion of the polymer film to the underlying substrate. Thus, the plasma coating process involves somewhat of a compromise between retention of monomer integrity in the plasma generated film and the strength of the adhesion between the coating and the solid substrate. In the case of biomedical devices and contact lenses, the adhesion and overall stability of the coating composition to the lens substrate is an extremely important consideration.

One method of applying the coating compositions to the substrate of the present invention is by pulsed plasma coupled with gradient layering. The duty cycle can be varied, thus creating variable duty cycle. The method can be used to maximize the adhesion of the coating composition and the functionalities present in the coating composition. Films deposited under low average power pulsed conditions tend to be more adhesive to a given substrate when compared to films deposited at the same average power but under CW operation. For a given average power, the momentary high peak power available under pulsed conditions assists in obtaining a stronger grafting of the film to the substrate than that obtained under the same average power CW condition. This stronger grafting under pulsed conditions is repeated with each plasma on cycle. The better grafting of the film to the substrate obtained under pulsed conditions can be even further enhanced by combining the pulsed deposition with a gradient layering technique. In this process, an initial high power, high plasma duty cycle is employed to graft the plasma generated coating composition tightly to the underlying substrate. The plasma duty cycle is subsequently progressively decreased in a systematic manner, with each decrease resulting in an increased retention of the C—O functionality in the coating. In this way, the successive plasma deposited films are tightly bonded to each other. The process is terminated when the exterior film layer has reached the desired composition. The succession of thin layers, each differing slightly in composition in a progressive fashion from the preceding one, results in a significantly more adhesive composite coating composition bonded to the substrate than coatings deposited without adjusting the deposition conditions under a relatively lower plasma duty cycle.

Gas-phase deposition, particularly plasma depositions, provide coating compositions of substantially uniform thickness. The thicknesses of the coating composition could be between 5 Å and 5 $\mu$m, more preferably between 50 Å and 1 $\mu$m, and most preferably between 100 Å and 0.1 $\mu$m. Using the RF pulsed plasma deposition provides linearity of the thickness of the coating composition with deposition time for a given plasma duty cycle and fixed monomer pressure and flow rate.

Samples to be coated (e.g., contact lenses) were located in the center of a 12-inch long, 4-inch diameter cylindrical glass reactor (i.e., substrates were placed directly in the plasma excitation zone). Despite the very low average power inputs involved under the pulsed plasma conditions, apparently the periodic relatively high peak powers employed during plasma on periods provide efficient grafting of the films to the substrate. The approach employed here can be contrasted with that involved with continuous-wave plasma polymerizations of crown ethers in which substrates were located upstream of the plasma electrodes (i.e., the active plasma zone) [E. E. Johnston, B. D. Ratner, and J. D. Bryers, "RF plasma deposited PEO-like surfaces that inhibit *Pseudomonas aeruginosa* accumulation," *Polym. Mater. Sci. and Engi.* (Abstracts), 77, p. 577 (1997); E. E. Johnston, B. D. Ratner and J. D. Bryers, NATO ASI Series E, Applied Science, Vol 346, pp.465–476, (1997)]. Furthermore, the present pulsed plasma approach obviates the need for a two-step process in which an initial high-power plasma discharge is employed to provide initial grafting of the film to the substrate [E. E. Johnston, B. D. Ratner, and J. D. Bryers, "RF plasma deposited PEO-like surfaces that inhibit *Pseudomonas aeruginosa* accumulation," *Polym. Mater. Sci. and Engi.* (Abstracts), 77, p.577 (1997)]. The pulsed plasma polymerization approach employed in this invention provides the necessary film adhesion to the substrates achievable via a simple one-step pulsed process.

Figure 2:
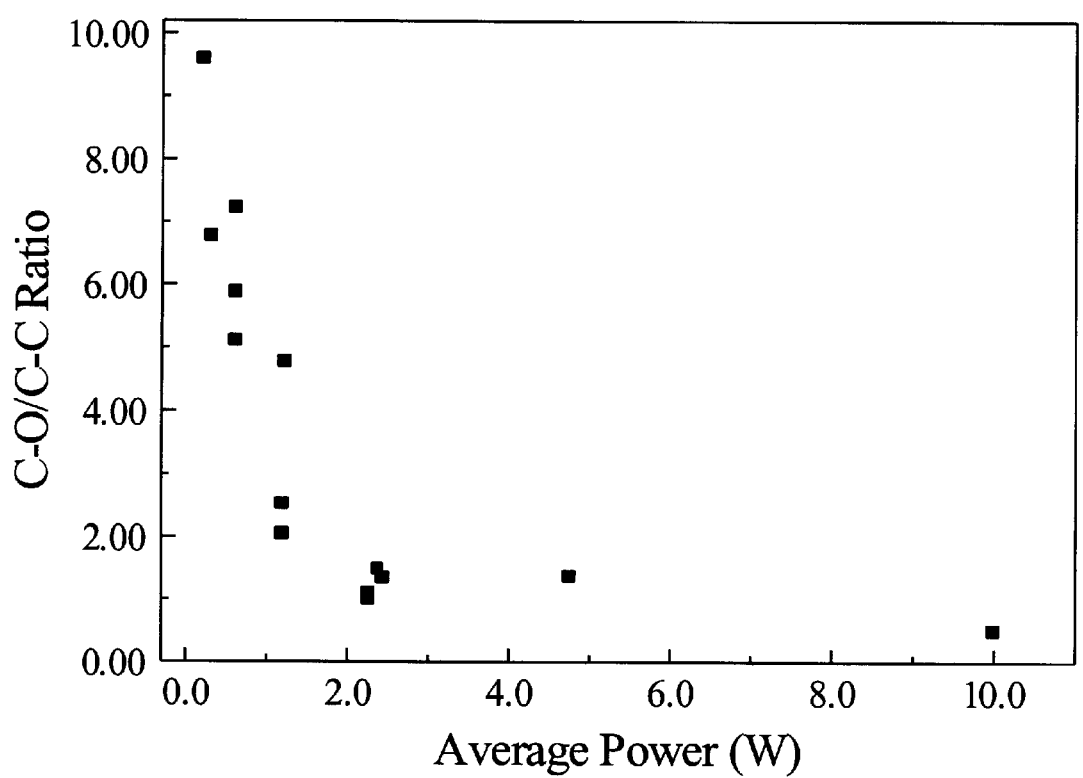
FIG. 2 shows variation of C—O/C—C ratio in the pulsed plasma polymerized 12-crown-4 films as a function of the average power employed during coating process.

A key aspect of the pulsed plasma polymerization approach is the fact that by permitting film formation to occur at ultra low average power inputs, it is possible to retain monomer functional groups in the plasma films to a much higher degree than that obtained under higher power continuous-wave conditions. This is of particular importance in the present case in that it is important to optimize the EO content of the films to provide maximum wettability and non-fouling properties to the plasma modified surfaces consistent with good adhesion of these films. The pivotal role of the average power input during plasma polymerization in dictating film compositions is illustrated clearly in FIGS. 1 and 2. FIG. 1 shows the high resolution C(1s) XPS spectra of films obtained from pulsed plasma polymerization of 12-crown-4 monomer at a series of plasma duty cycles. In this series, plasma on times were maintained at 0.1 ms and plasma off times varied from 1 ms to 12 ms, as shown. As shown in FIG. 1, the detailed curve-fitting analysis of the C(1s) XPS spectra reveal clearly a dramatic increase in the ether linkage content of the films (i.e., C—O peaks), relative to those observed for the C—C and C=O peaks, as the plasma off time was increased through the sequence 1, 2, and 4 ms. Further increases in plasma off times to 8 and 12 ms resulted in relatively little further changes in film compositions. Overall, the ether linkage retention in the films was observed to increase in a highly non-linear fashion with average power input as shown in FIG. 2. In this figure, the ratios of the integrated areas of C—O/C—C peaks obtained from the C(1s) XPS spectra are shown as a function of the average power input during film formation. The data represent runs carried out at a range of peak powers and plasma duty cycles. Of particular importance is the dramatic increase in the C—O film content (i.e., ether linkages) which become apparent at average power inputs of less than 2 W in a plasma reactor of approximately 2 L volume. The significance of this fact is that we were unable to maintain film deposition in this same plasma reactor with 1 2-crown-4 monomer at continuous-wave power inputs of less than 6 W, under identical flow and pressure conditions employed in the pulsed runs. Clearly, the pulsed plasma technique, by permitting extension of the plasma polymerization process to ultra average low power inputs, permits maximization of the EO content of the plasma deposited films. As documented in the examples which follow, the enhanced EO retention is important in terms of the resultant physical properties of these films, particularly those properties relating to wettability and biological non-fouling. Surprisingly, and in contrast with the CW results, it was observed that when the cyclic ethers were deposited under low duty cycle pulsed plasmas, the non-fouling coatings were of equal efficacy as those of the linear monomers.

The following examples are provided to further illustrate this invention and the manner in which it may be carried out. It will be understood, however, that the specific details given in the examples have been chosen for purposes of illustration only and not be construed as limiting the invention.

EXAMPLE 1

Figure 3:
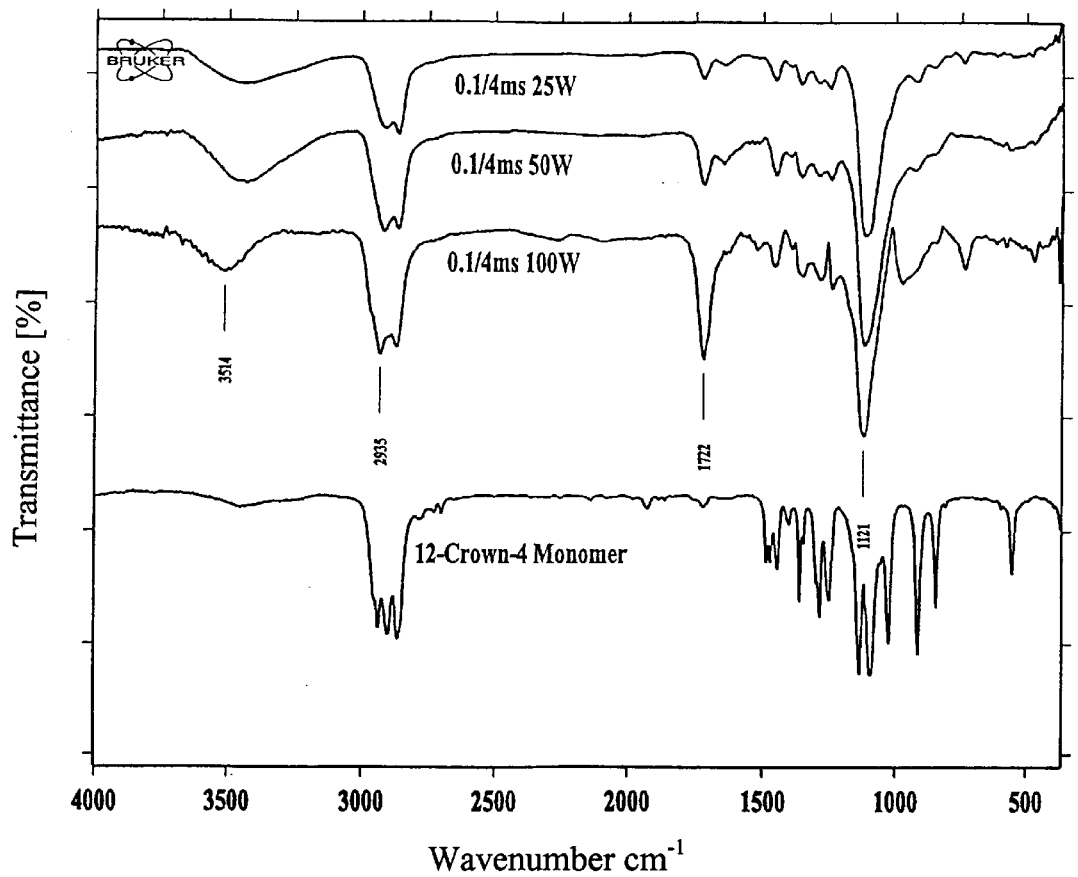
FIG. 3 shows an FTIR transmission spectra of a series of 12-crown-4 plasma polymeric films and 12-crown-4 monomer (bottom). The spectra reading from top to bottom are arranged in order of increasing peak powers employed during deposition at RF duty cycle of 0.1/4 ms.
Figure 4:
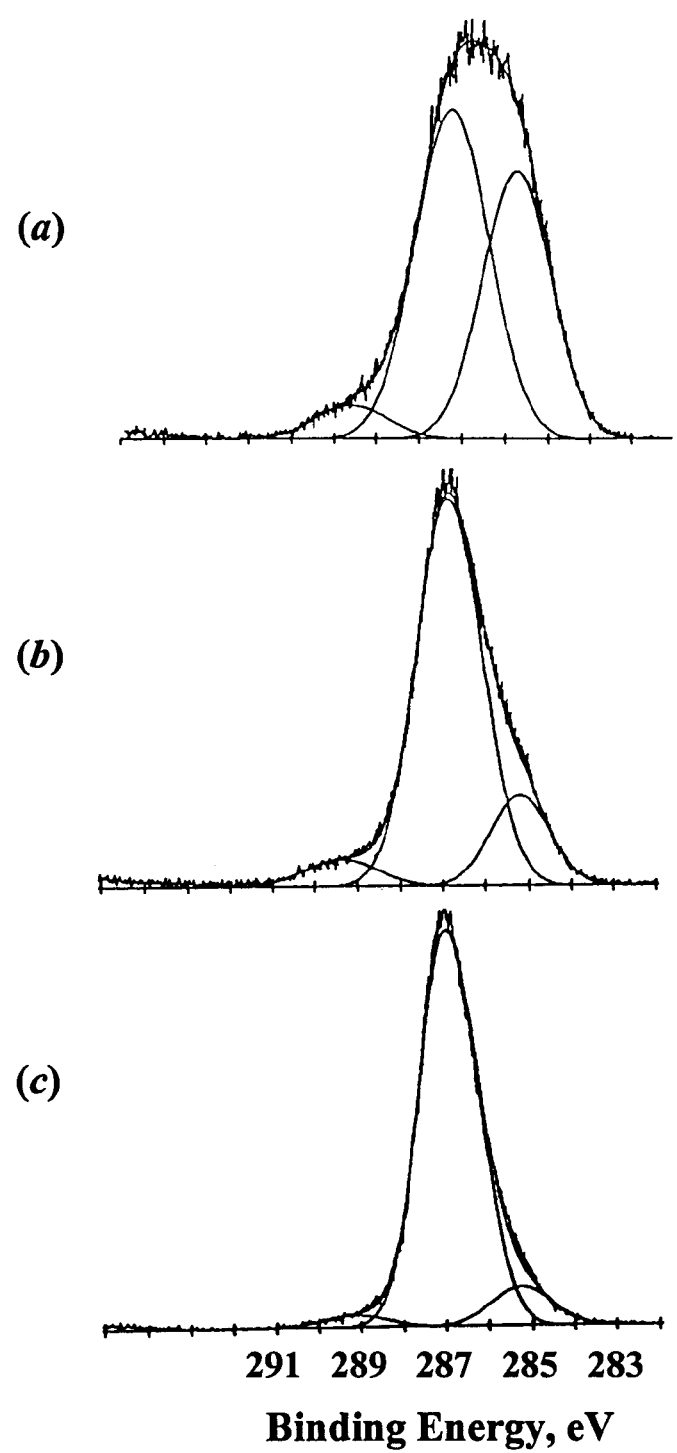
FIG. 4(a, b and c) show high resolution C(1s) XPS spectra of plasma polymerized 12-crown-4 films. RF duty cycle (on/off times or on/off ratio in ms) employed during formation of each film is 0.1/4 ms. The peak powers are: (a) 100 W; (b) 50 W; (c) 25 W, respectively.

12-Crown-4 monomer was plasma polymerized at a pulsed plasma duty cycle of 0.1 ms on and 4 ms off at peak power inputs of 25, 50, and 100 W. Substantial variations in film compositions were observed over this range of power inputs, as shown in FT-IR and C(1s) XPS spectra of these polymers (FIGS. 3 and 4, respectively). The FT-IR spectra show significant reductions in formation of —OH (3500 $cm^{-1}$) and C=O groups (~1700 $cm^{-1}$) with decreasing average power inputs during plasma operation. Neither of these groups is present in the starting monomer and their (undesired) formation occurs during plasma on periods. Thus, reducing peak power during plasma film formation sharply reduces the presence of these groups. Also, the FT-IR spectra reveal optimization of the C—O band at 1120 $cm^{-1}$ at low power input relative to other absorption bands (e.g., C—H, C=O, and —OH). XPS analyses of these films (FIG. 4) confirm the film composition changes noted in the FT-IR spectra in that a marked increase in C—O/C—C peak areas is observed with decreasing average power inputs.

EXAMPLE 2

Figure 5:
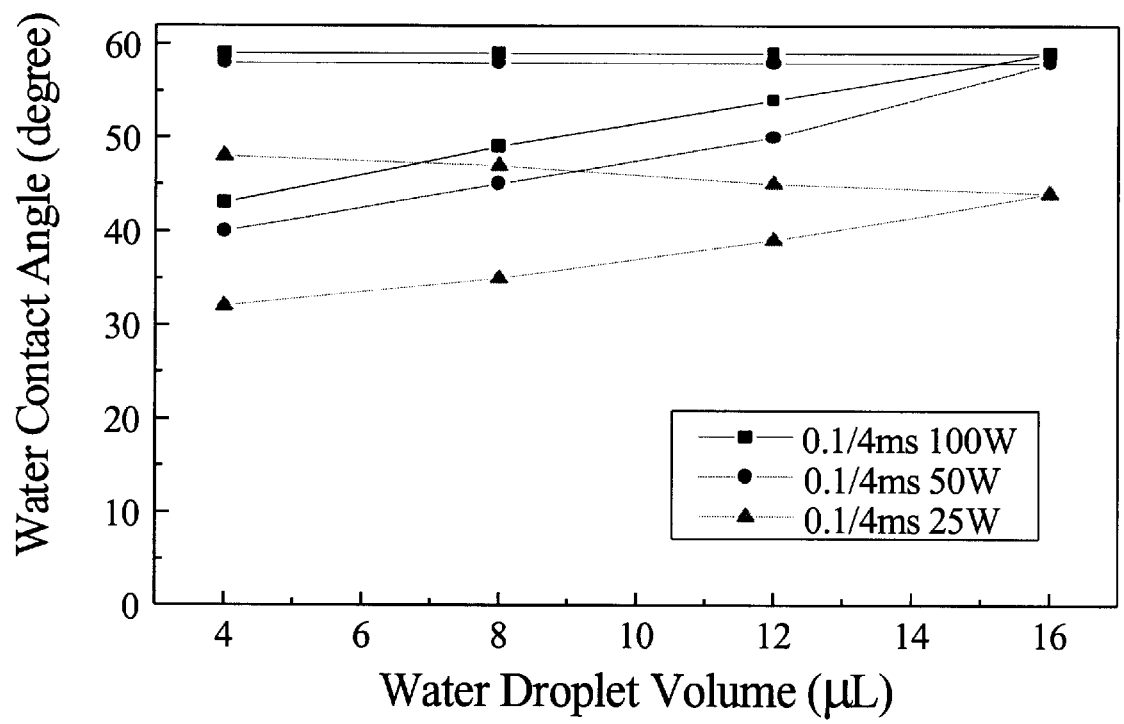
FIG. 5 shows water contact angle of pulsed plasma polymerized 12-crown-4 films as a function of RF peak power.

Advancing and receding water contact angles were measured for the same films described in Example 1. A substantial increased wettability of the films was observed for the run carried out at lowest power input (i.e., peak power 25 W) relative to the 50 and 100 W runs, as shown in FIG. 5.

EXAMPLE 3

Figure 6:
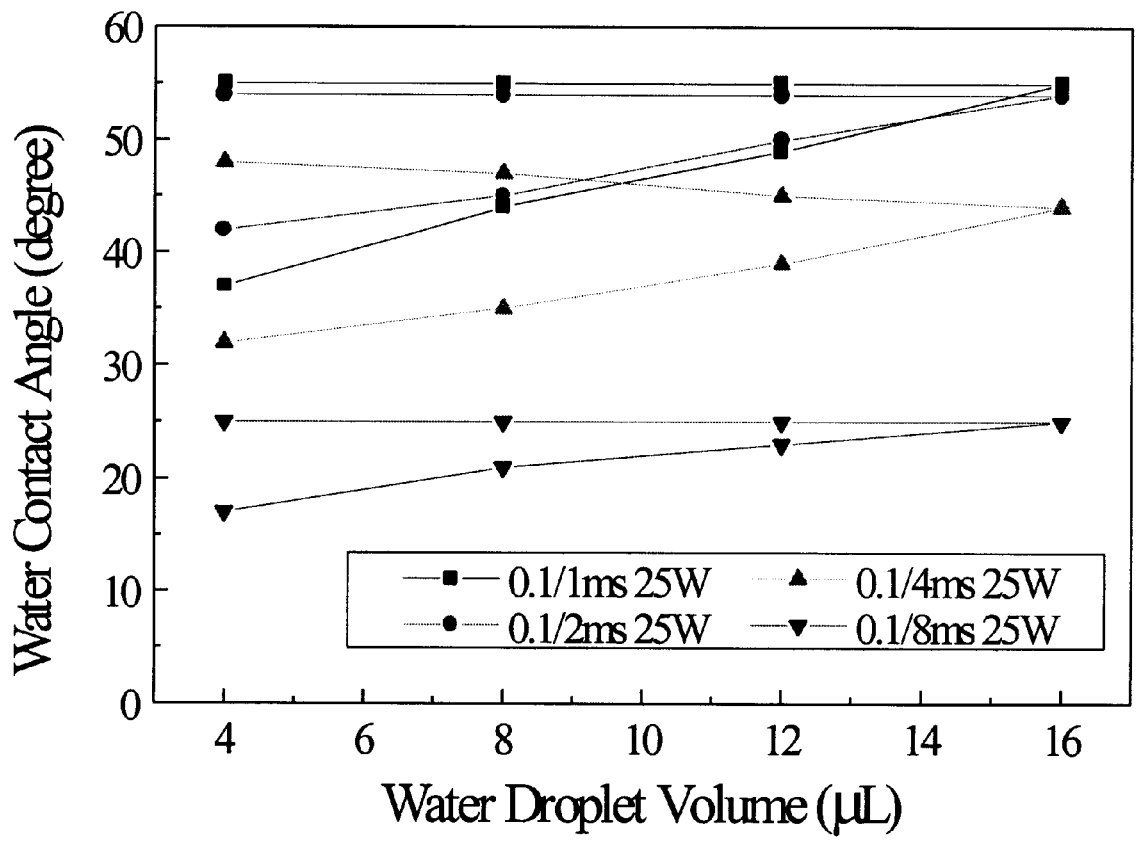
FIG. 6 shows water contact angle of pulsed plasma polymerized 12-crown-4 films as a function of the plasma off time under coating condition of plasma on time of 0.1 ms and RF peak power of 25 W.

Plasma polymers were synthesized from 12-crown-4 monomer at a constant peak power input of 25 W and pulsed plasma duty cycles (on/off times, in ms) of 0.1/1, 0.1/2, 0.1/4 and 0.1/8. Advancing and receding water contact angles were measured for films obtained in each of these separate runs. The results obtained are shown in FIG. 6. The wettabilities of the plasma generated films were observed to increase with decreasing pulsed plasma duty cycle employed during film formation, as evidenced by the decreasing water contact angles with decreasing duty cycle employed (FIG. 6).

EXAMPLE 4

Figure 7:
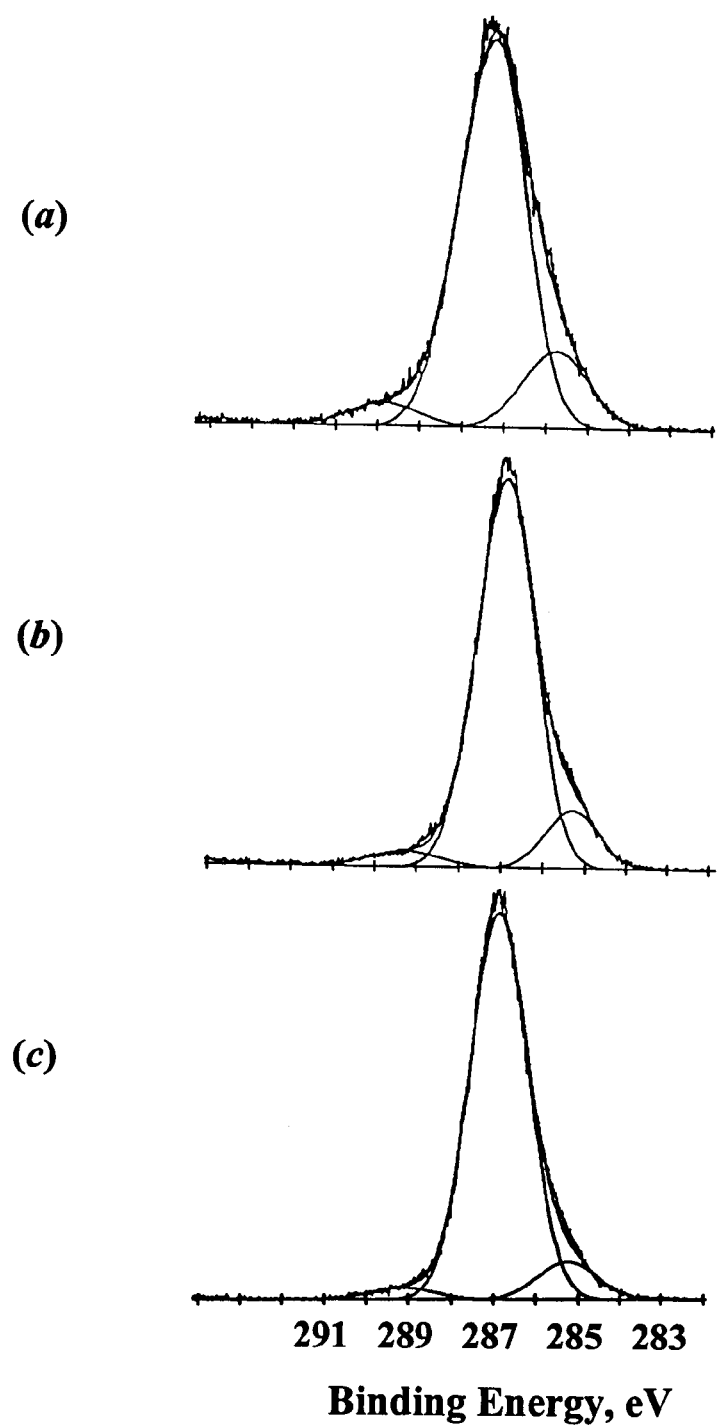
FIG. 7(a, b and c) show high resolution C(1s) ESCA spectra of 12-crown-4 films plasma polymerized at 25 W peak power. RF duty cycle (on/off times or on/off ratio in ms) employed during formation of each film are: (a) 10/400 ms; (b) 1/40 ms; and (c) 0.1/4 ms.
Figure 8:
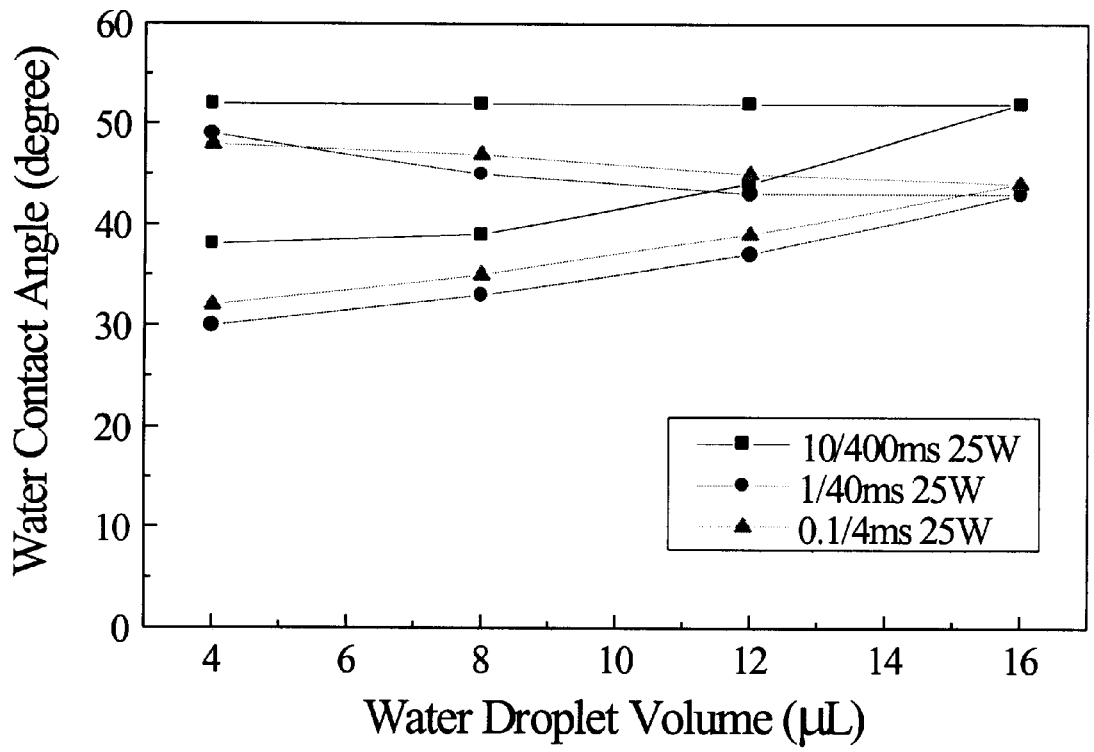
FIG. 8 shows the variation in water contact angle of pulsed plasma polymerized 12-crown-4 with changes in the plasma on to off pulsed width employed during deposition.

A series of pulsed plasma polymerized films were deposited from 12-crown-4 monomer at a constant duty cycle ratio of 1/40 (relative on to off times) and 25 W peak power input but with varying plasma pulse widths. The plasma on to plasma off times employed were 0.1/4, 1/40, and 10/400 ms. Relatively small film compositional changes and surface wettabilities were observed, as shown in FIGS. 7 and 8 by C(1s) XPS spectra and water contact angle measurements, respectively. The small compositional changes noted in these three runs, all carried out at an average power input of 0.61 W, reveal a slightly enhanced film EO content with decreasing plasma on and off pulse widths at constant overall duty cycles.

EXAMPLE 5

Figure 9:
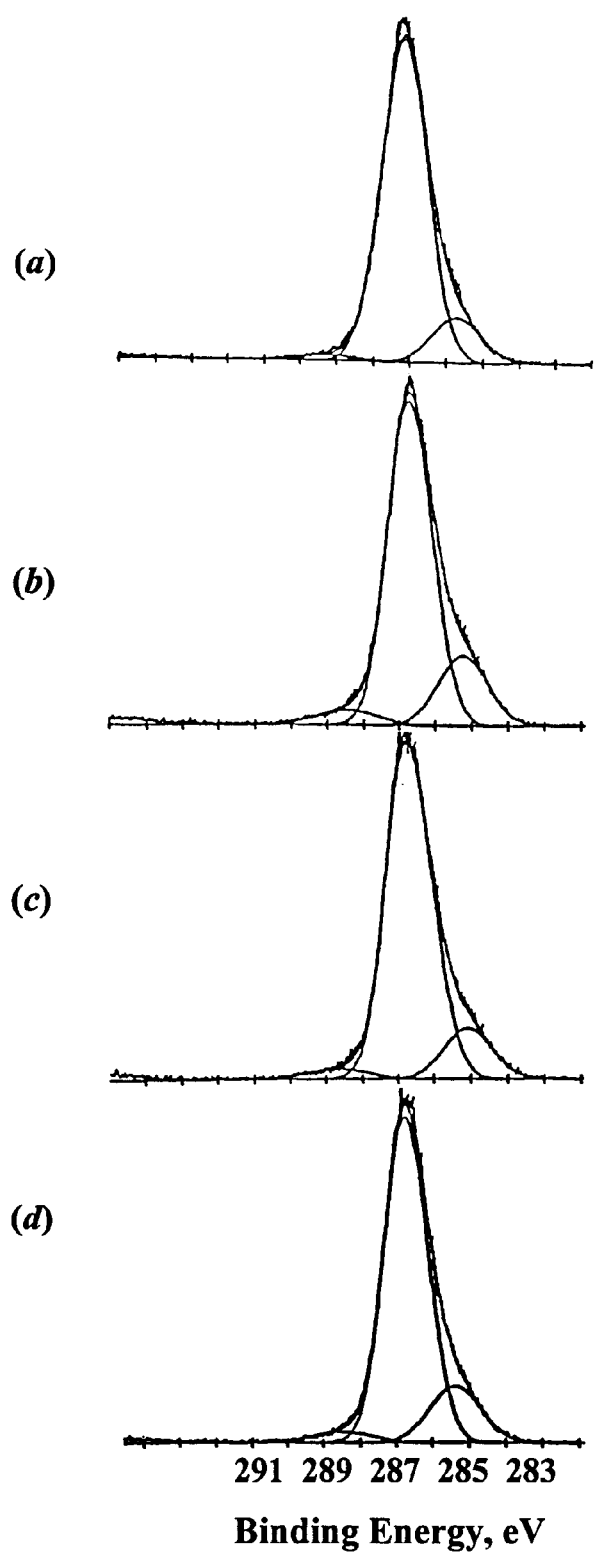
FIG. 9 shows a comparison of C(1s) XPS high resolution spectra of 12-crown-4 plasma deposited films obtained under coating condition 0.1/8 ms 25 W. (a) fresh sample, (b) after soaking in PBS at 37° C. for 15 days; (c) after exposure to PBS flow for 120 hours; and (d) after exposure to PBS flow for 240 hours.

The stability and adhesion of the pulsed plasma synthesized films from 12-crown-4 monomer, obtained over a range of average power inputs, were measured with respect to extended soaking in buffer at 37° C. and with respect to extended exposure to buffered flow solution. The plasma films were deposited on a variety of polymeric substrates, including PET disks and contact lenses. The surface compositions were determined by XPS and water contact angle measurements before and after the soaking and flow exposure experiments. Remarkably little changes were observed in film compositions after soaking and flow exposure, even in the case of films deposited at average power inputs as low as 0.31 W. For example, FIG. 9 shows the C(1s) XPS spectra of a plasma film deposited at a duty cycle of 0.1/8 ms on/off ratio and 25 W peak power as (a) freshly deposited film, (b) after soaking in PBS solution at 37° C. for 15 days, (c) after exposure to PBS flow for 120 hours, and (d) after exposure to PBS flow for 240 hours. Similarly, only relatively small changes in water contact angles were observed after those soaking and flow exposure tests. For example, an advancing water contact angle of 35° was obtained for films deposited at 0.1/8 ms, 25 W, after 240 hours of continuous exposure to PBS flow at 25° C. and a buffer flow rate of 30 ml/min.

EXAMPLE 6

Figure 10:
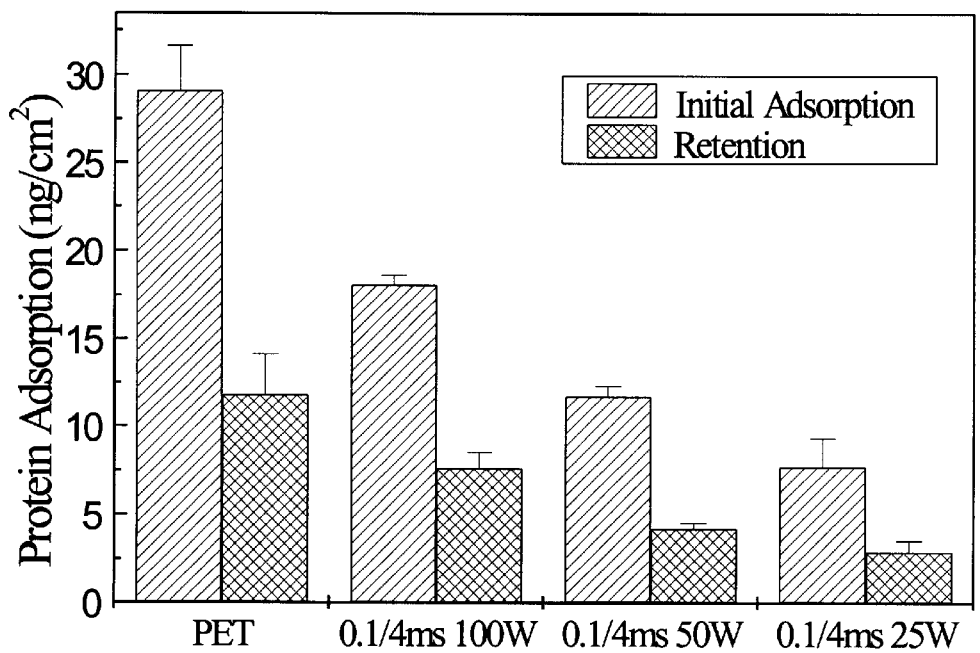
FIG. 10(a–b) show the variation in albumin absorption and retention of pulsed plasma polymerized 12-crown-4 as a function of: (a) RF peak power; and (b) plasma off time, and FIG. 11(a–b) show the variation in fibrinogen absorption and retention of pulsed plasma polymerized 12-crown-4 as a function of: (a) RF peak power; and (b) plasma off time.
Figure 10:
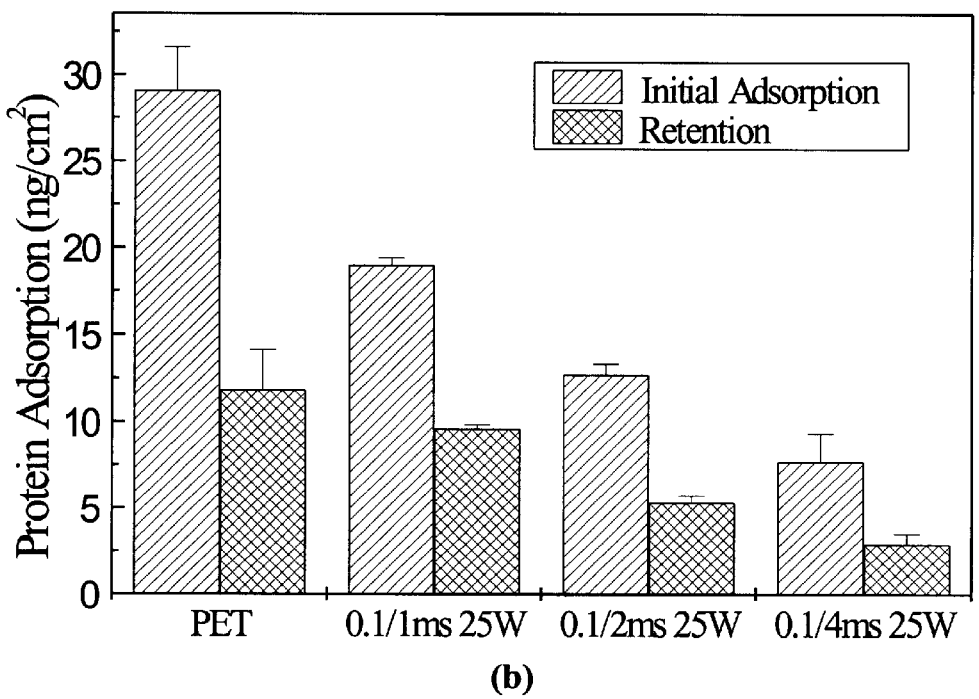
Figure 11:
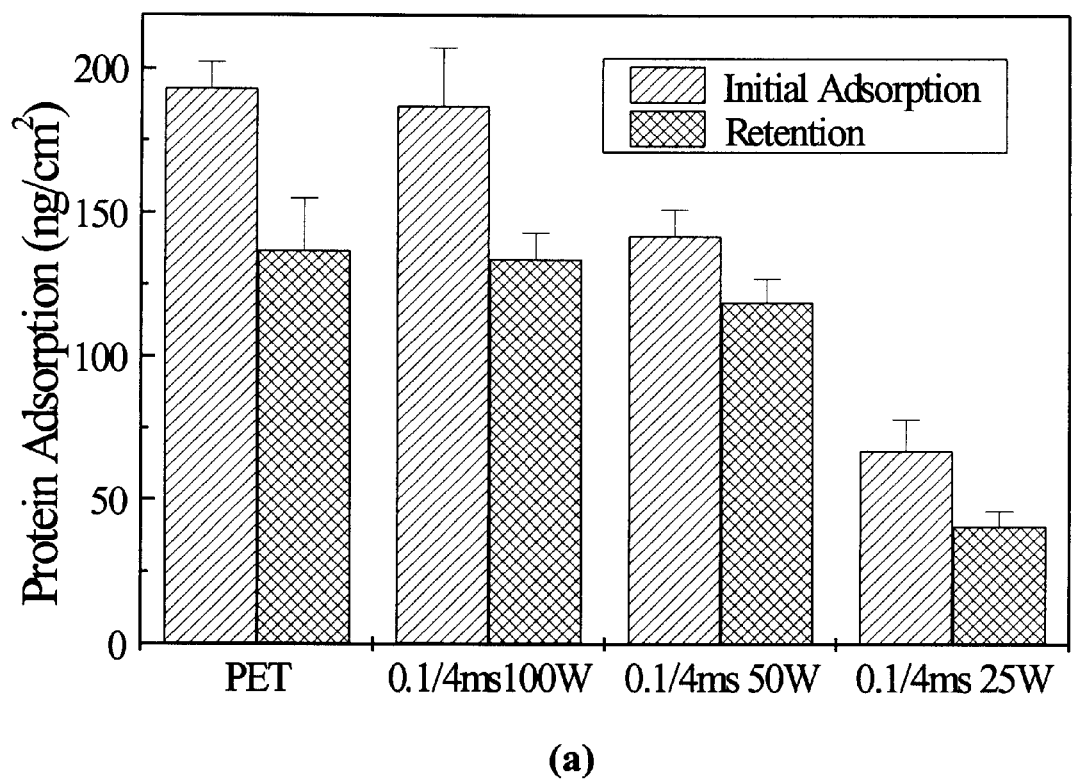
Figure 11:
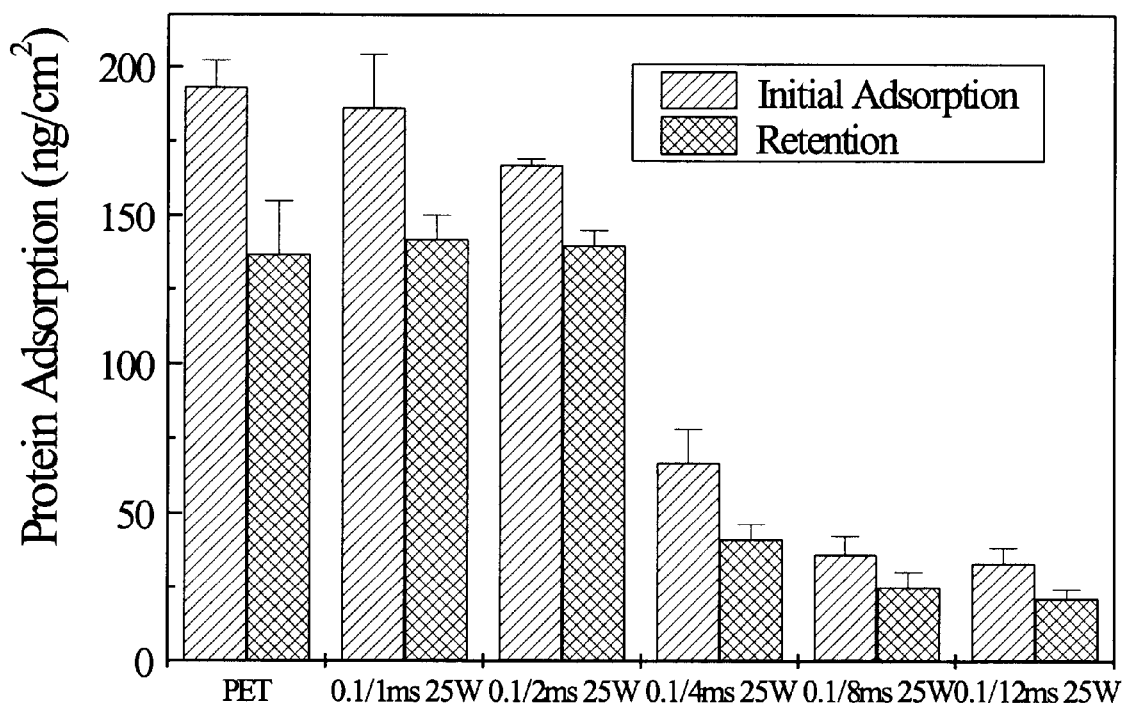

Protein absorptions were measured on a series of pulsed plasma polymerized films obtained from 12-crown-4 monomer at various plasma duty cycles. Protein adsorption measurements were carried out using $^{125}$I-radio-labeled albumin and fibrinogen proteins. Both initial protein adsorption and retention (i.e., protein resistant to removal by surfactant SDS wash) values were measured on films deposited on PET substrates. Uncoated PET substrates were employed as controls. Dramatic decreases in protein absorptions were observed on the pulsed plasma polymerized 12-crown-4 films versus that observed on the uncoated PET controls. Furthermore, progressively decreased protein adsorption was observed on the films as a function of the lowered plasma duty cycle (i.e., average power input) employed during film formation. The correlation between decreased protein adsorption and decreased power input during film formation is shown in FIGS. 10 and 11 for albumin and fibrinogen, respectively. The decreases in protein adsorption are very substantial on these crown ether films, ranging to reduction factors as high as 10 in the case of the lowest duty cycle deposited films (FIG. 11). Both the magnitude of the protein adsorption decreases and the strong dependence of protein adsorption on the average power input during plasma polymerization differ significantly for the pulsed plasma polymerized films of this investigation relative to that reported under continuous-wave conditions [E. E. Johnston, B. D. Ratner, and J. D. Bryers, "RF plasma deposited PEO-like surfaces that inhibit *Pseudomonas aeruginosa* accumulation," *Polym. Mater. Sci. and Engi.* (Abstracts); E. E. Johnston, B. D. Ratner and J. D. Bryers, NATO ASI Series E, Applied Science, Vol 346, pp. 465–476, (1997)].

EXAMPLE 7

Films pulsed plasma polymerized from crown ethers were shown to exhibit essentially no absorption of visible light. For example, the UV-visible absorption spectrum of a 200 nm thick film obtained from pulsed plasma polymerization of 12-crown-4 monomer at a duty cycle of 0.1/4 ms and 25 W peak power showed no noticeable film absorption over the wavelength range of 360 to 900 nm. Transparency of these films in the visible region of the electromagnetic spectrum is an important property of the films, particularly in applications such as coatings for contact lenses.

EXAMPLE 8

Plasma films deposited from the monomer dioxane were shown to contain EO units, with the density of EO units increasing as the plasma duty cycles employed during deposition were reduced. However, the C—O/C—C ratios obtained from C(1s) XPS analyses of these films remained substantially less than those obtained from polymerization of 12-crown-4 monomer under similar power, duty cycle, and flow conditions.

EXAMPLE 9

Plasma films obtained from 15-crown-5 monomer were shown to contain EO film densities at least as high as those obtained from 12-crown-4 monomer. However, the lower vapor pressure of this monomer resulted in very low film deposition rates. The deposition rates were increased by heating the monomer reservoir and all-gas inlet transfer lines.

The experiments above using pulsed plasma polymerizations of the cyclic ethers reveal the following:

(1). Highly effective non-fouling coatings can be obtained by pulsed plasma polymerization of the cyclic ether compounds when they are deposited at low plasma duty cycles. The efficacy of these films in preventing biomolecule adsorption is certainly equal to that observed with linear molecules, such as diethylene glycol divinyl ether ("EO2V"), triethylene glycol monoallyl ether ("EO3A") and the glymes; and (2). the non-fouling character of the pulsed plasma films improves sharply as the average power employed during deposition is decreased in cyclic ether films obtained via pulsed plasma polymerization.

An important aspect of pulsed plasma work is the marked increase in the C—O/C—C ratio of the plasma films as the average power employed during deposition is decreased. Remarkably, it was shown that films deposited at low average power (and thus containing high ether-linkage functional group density) exhibit exceptional stability towards soaking or even prolonged exposure to solution flow at an elevated temperature.

Although not intending to be bound by theory, it is hypothesized that this film stability reflects the strong film grafting to the substrate which is provided by the brief plasma on periods. In this way, film deposited during the plasma off period is anchored to the substrate during each successive plasma on period. Undoubtedly, the fact that the substrates are located in the active plasma zone between the RF electrodes aids in improving film stability. Thus, despite the use of low average power inputs, the pulsed plasma technique provides deposition of coatings having high ether content, strong adhesion, and excellent non-fouling properties.

In contrast with the experiments described above, the work reported [E. E. Johnston, B. D. Ratner, and J. D. Bryers, "RF plasma deposited PEO-like surfaces that inhibit *Pseudomonas aeruginosa* accumulation," *Polym. Mater. Sci. and Engi.* (Abstracts), 77, p. 577 (1997). E. E. Johnston and B. D. Ratner, "The effects of linear and cyclic precursors on the molecular structure of ether-rich plasma-deposited films," *Mater. Res. Soc.* (Abstracts), p. 464, December 1998 (Boston, Mass.); E. E. Johnston, B. D. Ratner and J. D. Bryers, NATO ASI Series E, Applied Science, Vol 346, pp. 465–476, (1997)] located their substrates upstream of the plasma discharge zone. Undoubtedly, this was done to enhance the ether content of the films. However, preliminary experiments have indicated that films deposited under low power CW conditions outside the active plasma region exhibit relatively poor stability.

What is claimed is:

1. A method for plasma depositing a coating to a solid substrate, said method comprising:

subjecting a macrocycle to a gas phase polymerization utilizing a pulsed discharge, said macrocycle containing at least one hetero atom, wherein said hetero atom is oxygen, nitrogen or sulfur, and wherein said coating is non-biologically fouling, thereby imparting a property of reduced protein adsorption.

2. The method of claim 1, wherein said macrocycle is a cyclic ether.

3. The method of claim 1, wherein said macrocycle is 12-crown-4, 15-crown-5, 18-crown-6, or a mixture thereof.

4. The method of claim 1, wherein said pulsed discharge has a duty cycle of less than about $1/5$, in which the pulse-on time is less than about 100 msec and the pulse-off time is less than about 2000 msec.

5. The method of claim 1, wherein said pulsed discharge has a duty cycle of from about $1/10$ to about $1/1000$, and the pulse-on time is from about 1 $\mu$sec to about 100 msec, and the pulse-off time is from about 10 $\mu$sec to about 2000 msec.

6. The method of claim 1, wherein said substrate is a contact lens or a biomaterial.

7. The method of claim 1, wherein said gas phase polymerization is high voltage discharge, radio frequency, microwave; ionizing radiation induced plasma polymerization; photo induced polymerization; or a combination thereof.

8. The method of claim 1, wherein said pulsed discharge comprises a series of variable duty cycle.

9. The method of claim 1, wherein said substrate is located in the active plasma zone during said gas phase polymerization.

10. The method of claim 1, wherein said pulsed discharge utilizes an average power inputs of less than about 3 W per liter of plasma reactor.

* * * * *

UNITED STATES PATENT AND TRADEMARK OFFICE
CERTIFICATE OF CORRECTION

PATENT NO. : 6,329,024 B1
APPLICATION NO. : 09/316620
DATED : December 11, 2001
INVENTOR(S) : Richard B. Timmons and Yuliang Wu It is certified that error appears in the above-identified patent and that said Letters Patent is hereby corrected as shown below:

In the Specification

At Col. 1, line 15, delete

"The U.S. Government has certain rights in the present invention pursuant to the National Institutes of Health under Grant #R01AR43186 and by the Texas Higher Education Coordinating Board ATP Program under Grant #003657-137."

At Col. 1, line 15, add

--This invention was made with U.S. Government support under Grant #R01AR43186-01 awarded by the National Institutes of Health and under Grant #003656-137 awarded by the Texas Higher Education Coordinating Board ATP Program. The government has certain rights in this invention.--

Signed and Sealed this
Twelfth Day of August, 2014

Michelle K. Lee
*Deputy Director of the United States Patent and Trademark Office*